United States Patent [19]
Friend et al.

[11] Patent Number: 5,928,219
[45] Date of Patent: Jul. 27, 1999

[54] FAIL-SAFE NEEDLE GUIDE MOUNT FOR ULTRASONIC PROBES

[75] Inventors: Philip J. Friend, Seattle; Marc W. Bommarito, Maple Valley; Matthew F. Willkens; Andrew L. Walston, both of Seattle, all of Wash.

[73] Assignee: Siemens Medical Systems, Inc., Iselin, N.J.

[21] Appl. No.: 09/163,048

[22] Filed: Sep. 29, 1998

[51] Int. Cl.$^6$ .................................................. A61B 17/00
[52] U.S. Cl. ............................................... 606/1; 600/462
[58] Field of Search ...................... 606/1, 169; 600/437, 600/446, 462, 471; 604/72

[56] References Cited

U.S. PATENT DOCUMENTS

| | | | |
|---|---|---|---|
| 4,638,799 | 1/1987 | Moore | 606/1 |
| 4,682,593 | 7/1987 | Johnson | 606/1 |
| 5,817,117 | 10/1998 | Cartaxo | 606/1 |
| 5,820,623 | 10/1998 | Ng | 606/1 |

*Primary Examiner*—Michael Buiz
*Assistant Examiner*—Kevin Truong
*Attorney, Agent, or Firm*—Jeffrey Slusher

[57] ABSTRACT

A needle guide mount has a main guide body, with a knob arm and a pivot arm each attached at one end to the main guide body. A gate assembly is pivotably in the pivot arm and has an open position, in which the gate assembly can pivot freely away from the knob arm, and a closed position, in which the gate assembly is secured in the knob arm. The gate assembly preferably has a shaft, a knob that can move longitudinally and rotatably on the shaft, and a locking arrangement that permits the gate assembly to enter the closed position only when the central axis of the gate assembly lies less than a predetermined maximum misalignment angle away from a correct mounting alignment axis. If the guide mount is not properly positioned on the probe, then the gate assembly is out of correct alignment and the locking arrangement is unable to engage. The operator can then easily feel that she is not able to mount the guide. The gate assembly preferably also has a contact member that contacts an outer surface of the probe and urges the gate assembly out of alignment when the needle guide mount is in an incorrect orientation relative to the probe. A protrusion and an indentation are also preferably provided on the guide mount and probe. If the needle guide mount is incorrectly positioned, then the protrusion urges the gate assembly out of alignment with the alignment axis.

6 Claims, 6 Drawing Sheets

FAIL-SAFE NEEDLE GUIDE MOUNT FOR ULTRASONIC PROBES

BACKGROUND OF THE INVENTION

1. Field of the Invention

This invention involves a needle guide mount for attachment to an ultrasound probe.

2. Description of the Related Art

Many surgical procedures involve inserting a needle or cannula into a patient while viewing an image of the region of insertion. These include such procedures as needle biopsy, drainage, amniocentesis, precision injections, cell aspiration, and radio-frequency cauterization. For example, ultrasonic imaging is often used to guide the insertion of a biopsy needle in order to more accurately obtain a tissue sample from a region of interest. Such image-aided needle insertion may also be helpful when one wants to inject or extract a fluid into or from a precisely defined place within the patient.

During these procedures, an ultrasonic probe is held against the patient's body, usually along with some coupling agent. An image of the area of the body adjacent to or near the probe is then created and displayed using conventional ultrasonic imaging techniques while the physician inserts the needle and guides it towards its target. At least portions of both the needle and the target are visible on the display.

Often, the physician mounts a needle guide on the transducer probe while continuing to watch the display screen—looking away from the screen might cause him to move the probe and thus lose the image of the target. He then assumes that the needle, once inserted, will follow a course along or between one or more guide lines that are displayed on the display screen.

Many needle guides, however, can mount onto the probes with different orientations. For example, if the probe has a circular cross section and the needle guide has a circular clamp-like mounting arrangement, then the needle guide could end up with an angular position far from the proper position. Even probes with non-circular cross-sections can have two or more "secure" mounting positions, only one of which will be correct. For example, a probe with a substantially rectangular cross-section might allow mounting of a needle guide on either of the two short sides. If the physician, while watching the display screen, accidentally mounts the needle guide with an incorrect orientation and then inserts the needle, then the needle will penetrate the wrong part of the patient's body. The disadvantages of such a potentially grave error should be obvious to even the most stoic who imagine themselves the hapless, cringing recipients of such an incorrect needle insertion.

Conventional arrangements all fail either to clamp the needle guide to the probe securely, or to do so in a such a way as to eliminate the risk that the guide will be mounted with the wrong orientation. What is needed is a needle guide that can be both securely mounted on a probe only when it provides the correct needle orientation.

SUMMARY OF THE INVENTION

The invention provides such a needle guide mount for mounting a needle guide on an imaging probe. The needle guide mount according to the invention has a main guide body, with a knob arm and a pivot arm each attached at one end to the main guide body. A gate assembly is pivotably mounted at a pivot point in the pivot arm and has an open position, in which the gate assembly can pivot freely away from the knob arm, and a closed position, in which the gate assembly is secured in the knob arm.

The gate assembly in the preferred embodiment has a shaft, a knob that can move longitudinally and rotatably on the shaft, and a locking arrangement that permits the gate assembly to enter the closed position only when the central axis of the gate assembly lies less than a predetermined maximum misalignment angle away from a correct mounting alignment axis.

The locking arrangement preferably comprises a threaded post member mounted on the shaft, and a mating, threaded surface on an inner portion the knob. The threaded surface of the knob extends to and engages the threaded post member only when the gate assembly lies less than the predetermined maximum misalignment angle away from the correct mounting alignment axis.

In the preferred embodiment, the knob arm has a substantially circular opening positioned so that the alignment axis extends substantially through the center of the opening. The knob preferably has at least two portions: an outer portion, which is larger than the opening, and the inner portion, which is smaller than the opening. When the gate assembly is in the closed position, the outer portion then seats against the knob arm and within the opening.

To further ensure mounting only when the guide mount is properly positioned and aligned, the guide mount according to the invention preferably also has a contact member mounted on the shaft that contacts an outer surface of the probe and urges the gate assembly out of alignment with the alignment axis only when the needle guide mount is in an incorrect orientation relative to the probe.

As yet another safeguard against improper mounting, the needle guide and the probe preferably also are provided with a protrusion (on the guide or probe) and indentation (on the probe or guide, depending on which has the protrusion). The protrusion mates with the indentation only when the needle guide mount is in a correct orientation relative to the probe. If the needle guide mount is incorrectly positioned, then the protrusion urges the gate assembly out of alignment with the alignment axis.

DETAILED DESCRIPTION

Figure 1:
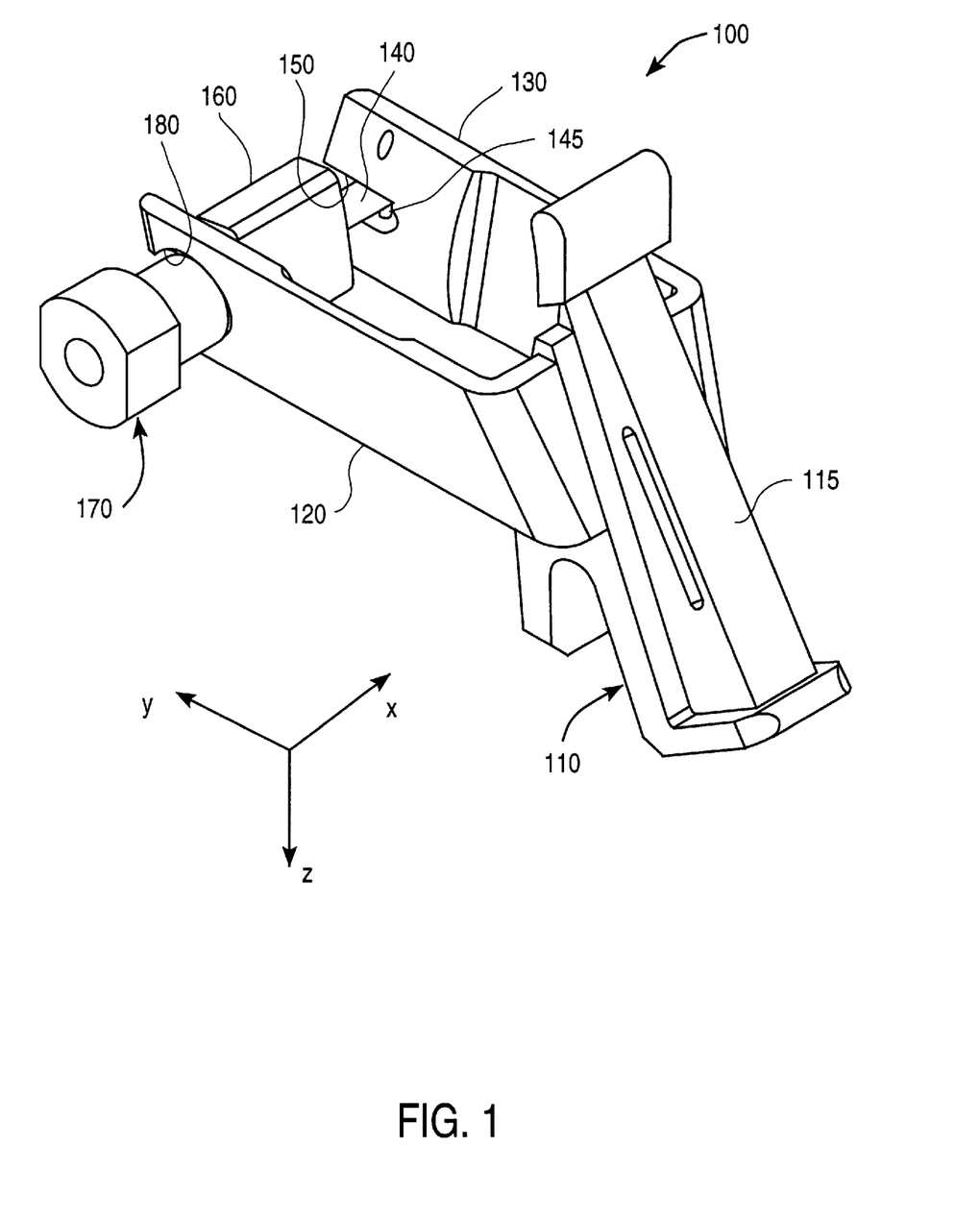
FIG. 1 is a perspective view of a preferred embodiment of a needle guide mount according to the invention.

FIG. 1 shows the main parts of the needle guide according to the invention in the closed configuration it would have when mounted properly on a probe. A main body 110 includes a supporting surface 115 on which any conventional, detachable needle holder (not shown) may be mounted. Such needle holders typically include at least one guide channel through which the surgeon inserts a biopsy or other needle to guide it into a patient. Since many needle holders that would be suitable for use with the invention are widely known and used, they are not described further here. The purpose of the needle guide 100 is thus to ensure that the main body 110 and thus the supporting surface 115 are mounted securely, with a known, fixed orientation, on the probe.

The needle guide includes two arms—a knob arm 120 and a pin arm 130—which are mounted in the main body using any known method such as being press-fitted onto mounting pins, or by soldering. It is also possible for the arms 120, 130 to be manufactured together with the main body as a unit, although this will in general be unnecessarily complicated and expensive, especially since these parts are preferably made of autoclavable materials such as stainless steel. The inner surfaces of the arms 120, 130 are designed and manufactured using known techniques so that they conform to the outer mounting surface of whatever probe the needle guide is intended to be used on, although they extend mainly parallel to each other.

A shaft 140 is mounted on a pivot pin 145 in a slot-like opening 150 in the free end of the pin arm 130. When mounted on a transducer, the arms 120, 130 extend mainly in a horizontal plane, that is, in the X-Y plane indicated by the coordinate system included in FIG. 1. The pivot pin 145 extends mainly vertically, that is, in the Z-direction, so that the shaft 140 thus pivots mainly in the horizontal plane.

Figure 6:
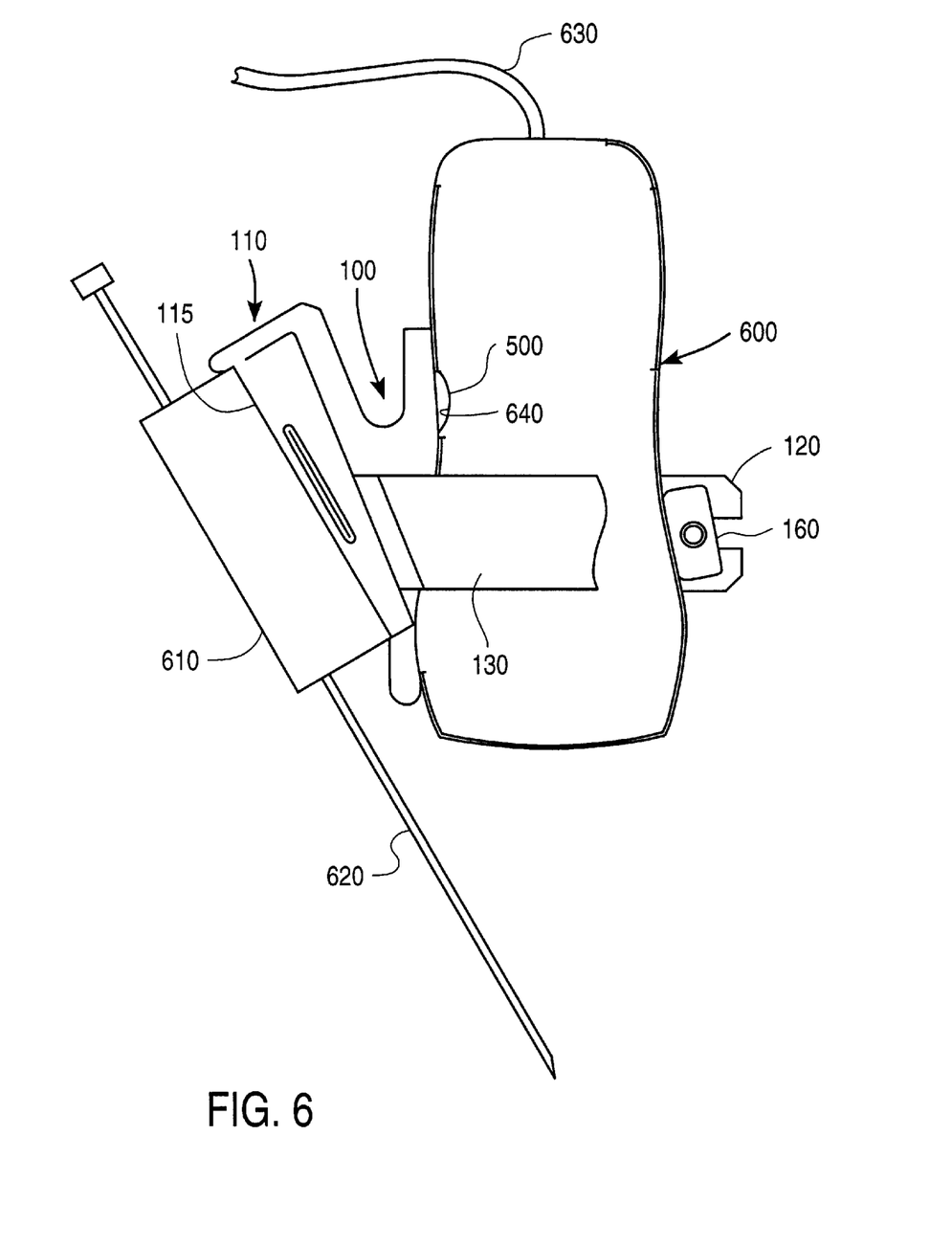
FIG. 6 shows the needle guide mount according to the invention actually mounted on a transducer probe, along with a needle guide and a needle.

A pivot block 160 is securely mounted on the shaft 150 and is between the arms 120, 130 when the needle guide mount is in the closed position shown in FIG. 1. As is illustrated in FIG. 6 and explained further below, the pivot block also forms a contact member whose inner surface is preferably shaped to touch and conform to the adjacent surface of the transducer probe to further ensure that the needle guide can be mounted only in the proper position and orientation on the probe.

A knob 170 is mounted on a shaft (see below) and can move toward and away from the pivot block 160. The knob is also free to rotate on the post. As FIG. 1 shows, when the needle guide mount is in the closed position, the knob arm 120 extends between the knob 170 and the pivot block 160. In the closed position, the pivoting gate assembly, which includes the knob, the pivot block and the shaft connecting the two, rests and is secured in an opening 180 in the end of the knob arm 120.

Figure 2:
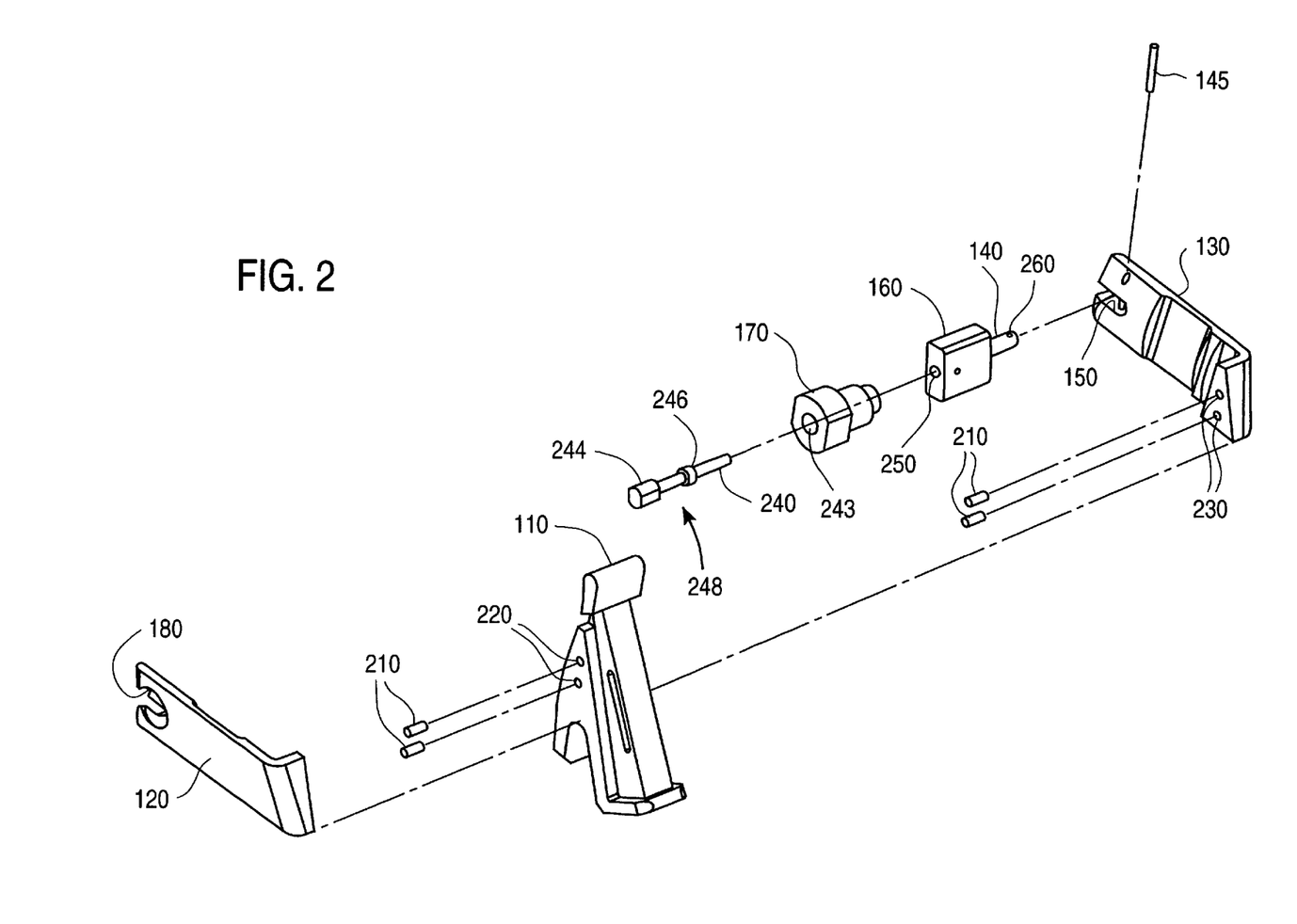
FIG. 2 is an exploded view of the needle guide mount of FIG. 1.

FIG. 2 is an exploded view of the needle guide mount 100 shown in FIG. 1. As FIG. 2 shows, the arms 120, 130 are preferably mounted on the main body 110 by means of dowels 210 that are press-fit into mating holes 220, 230 in the main body 110 and the attached ends of the arms 120, 130, respectively.

FIG. 2 also shows the shaft 240, which extends through a hole 243 formed axially through the mainly cylindrical knob 170. The shaft 240 is secured in the pivot block 170, for example by soldering its end in a hole 250 made in the pivot block 170. Mounted securely on the end opposite the pivot block 170, the shaft 240 has a head 244, which is not able to pass all the way through the axial hole 243, but rather only into the outer part of it. When the shaft 240 is inserted through the hole 243 and is secured in the pivot block 160, the knob 170 can thus move toward and away from the pivot block, but is captured by the head 244. A threaded, sleeve-like post 246 is secured on the shaft 240 between the head 244 and the end of the shaft secured in the pivot block. The shaft 240, head 244 and post 246 are referred to collectively below as the post member 248. FIG. 2 also shows the vertically extending hole 260, through which the pin 145 is inserted to hold the end of the shaft 140 in the pivot arm 130.

Figure 3:
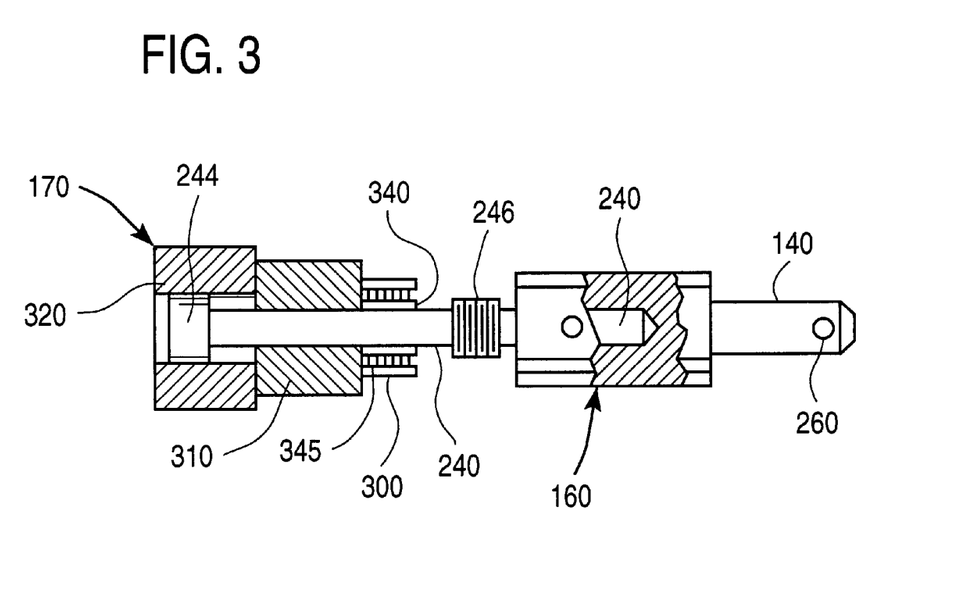
FIG. 3 is a partially cut-away view of a pivoting gate assembly used in the invention.

FIG. 3 shows the shafts 140 and 240, the pivot block 160, the knob 170, the threaded post 246, the pivoting assembly in greater detail. The pivot block 160 is shown partially cut-away to show that the shaft 240 is secured within the block. Also, FIG. 3 shows that the knob 170 in the preferred embodiment of the invention has an inner portion 300, a middle portion 310, and an (optional) outer portion 320, with increasing diameters or, if chosen not to be cylindrical, with increasing greatest axial length. This provides a relatively large-diameter outer portion that will be easy to grasp and turn, an inner portion with a small enough diameter to fit within the opening 180, and a middle portion with a diameter great enough to provide enough friction against the arm when the knob is screwed down onto the post 246. Furthermore, shaping the three portions of the knob mainly as cylinders makes the knob easy to machine. The outer portion, as FIG. 1 illustrates, may, however, be partially flattened or textured in order make it easier to grasp and turn. The three portions of the knob are shown in cross-section in FIG. 3 to illustrate how the head 244 at the end of the shaft 240 allows the knob to move toward and away from the post while still remaining captured on the shaft.

Having a right-angled step between the middle and inner portions helps ensure constant and known offsets and distances when the gate assembly is in a closed position (see below). The middle and outer portions of the knob may, however, be combined into a single constant-diameter portion, or they may be a single cone-shaped or otherwise curved portion of the knob.

The interior (surrounding the shaft 240) of the inner portion 300 is preferably provided with threads 345 to be able to mate with the externally threaded post 246. The surface of the inner portion 300 of the knob is labeled as the surface 340. Mating threads on the inner surface of the inner knob portion and on the post 246 are preferred for securing the knob because they are easy to make yet are secure. Other arrangements are, however, also possible. For example, the head 244 could have external threading, with mating threading on the interior of the outer portion 320 of the knob. The interior of the middle portion 310 could then have a diameter larger than that of the head to allow in-and-out movement of the knob. In general, however, such a knob will be harder to machine. Regardless of the arrangement, however, there will be some member like the post 246 that receives and locks the knob when the gate assembly as a whole is properly aligned.

As yet another alternative, the inner portion 300 of the knob could be provided with external threading that mates with internal threading provided in the pivot block 160. This would eliminate the need for a separate post 246.

Figure 4A:
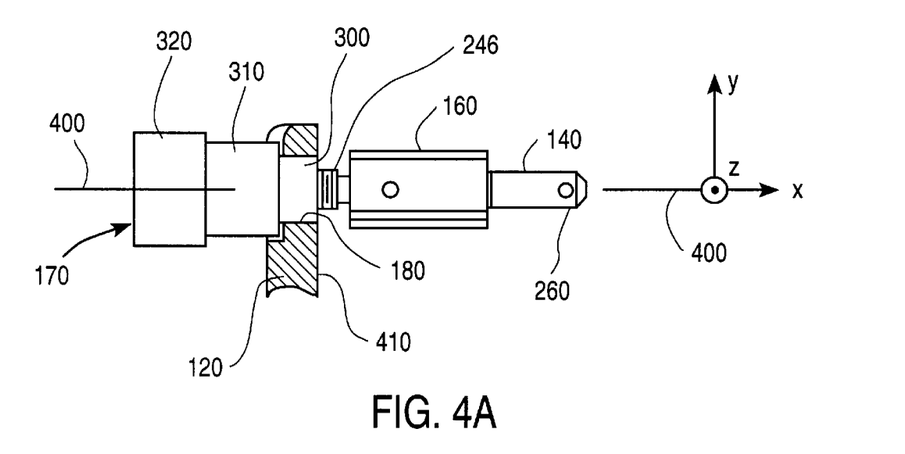
FIGS. 4A, 4B and 4C show the gate assembly in a closed, secured position, an open, aligned position, and an open, non-alignment position, respectively.

FIG. 4A shows the gate assembly in a closed, secure position, viewed from above, that is, in the Z-direction. The tip of the knob arm 120 is shown in cross section. In this closed position, the central axis 400 of the assembly, in particular, of the shaft 140 and the cylindrical inner portion 300 of the knob 170, is coincident with the X-axis (see FIG. 1), that is, with a line extending from the pivot point of the shaft 140 on the pin 145 (see FIG. 2) and the center of the circular opening 180. In the closed position, the inner portion 300 seats within the opening 180. Note that the central axis of the substantially cylindrical opening preferably coincides with the X-axis. The inner portion 300 and the opening 180 preferably have substantially the same diameter in order to eliminate any potential gaps, wobble, and possible resulting misalignment.

As FIG. 2 shows, the rear-facing opening 180 preferably takes up more than 180-degrees of arc of the tip of the arm 120. In other words, at the rearmost surface of the arm 120, the opening 180 is smaller, viewed vertically, than it's greatest diameter. When the gate assembly is in the closed position, this provides positive locking of the inner portion 300 of the knob in the opening, in addition to the force of friction exerted by the wider, middle portion 310 on the outer surface of the arm 120.

Figure 4B:
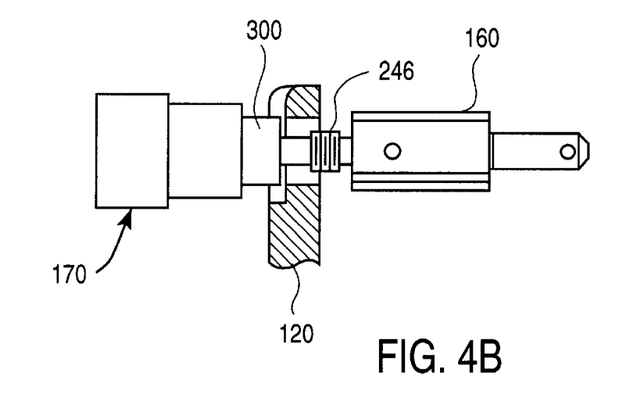

FIG. 4B shows the assembly in a free, open position. In this position, the knob 170 has been turned so that the inner portion 310 is screwed off of the threaded post 246, and has been pulled away from the post 246. The opening 180 is open at the very end of the knob arm 120 to allow the gate assembly to pivot about the Z-axis. The gate assembly can thus be swung preferably completely out from the space between the two arms 120 to allow the entire mount to be fitted over one side of and around a transducer probe.

Figure 4C:
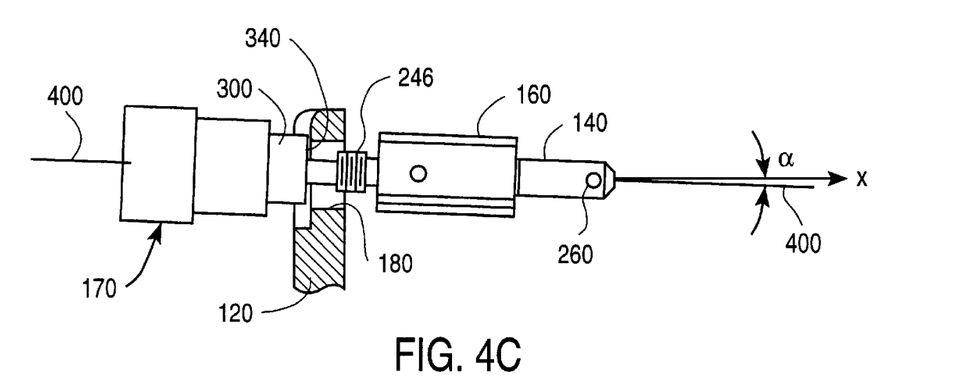

In FIG. 4C, the gate assembly is in the open position, so that the inner surface 340 of the knob clears the opening 180 in the tip of the arm 120, but for some reason the central axis 400 of the gate assembly is out of alignment with the X-axis by some small angle α. In this position, the inner portion 300 of the knob cannot extend into the opening 180 and engage the post 246, since it will be blocked by contact with the tip of the arm 120. Only when the angle α is small enough will the knob be able to enter the opening 180 and engage the post 246. The closeness of the fit between the outer surface of the inner portion 300 of the knob and the inner surface of the opening, that is, the difference in their diameters, or the amount of "gap" or tolerance, will determine what maximum angle a will still permit the knob 170 to engage the post 246. In one prototype of the invention used on a transducer probe of a typical size, an alignment "error" of as little as α<1.5 degrees was enough to make mounting of the needle guide mount onto the probe impossible.

In many applications, a maximum misalignment or error angle α of five or even more degrees may be acceptable. As is explained below, there are several types of incorrect mounting that can cause the gate assembly to pivot beyond the maximum angle α, and a mating tab/indentation arrangement is preferably provided on the mount and transducer probe that will prevent the gate assembly from getting closer to alignment than the maximum angle even for otherwise cylindrical or symmetrical probes. The maximum angle a will therefore depend on the geometry of the probe in any given application and can be determined by normal experimentation and design techniques.

The maximum for the angle a can be determined using conventional geometrical calculations and testing, and will in many cases depend on the geometry of the probe on which the needle guide mount according to the invention is mounted. For example, the wider (in the X-direction) the probe is, the greater the distance will be between the pivot point 260 and the innermost surface 410 (FIG. 4A) of the knob arm 120, and the greater will be the lateral offset of the knob per unit of angle for α.

Figure 5:
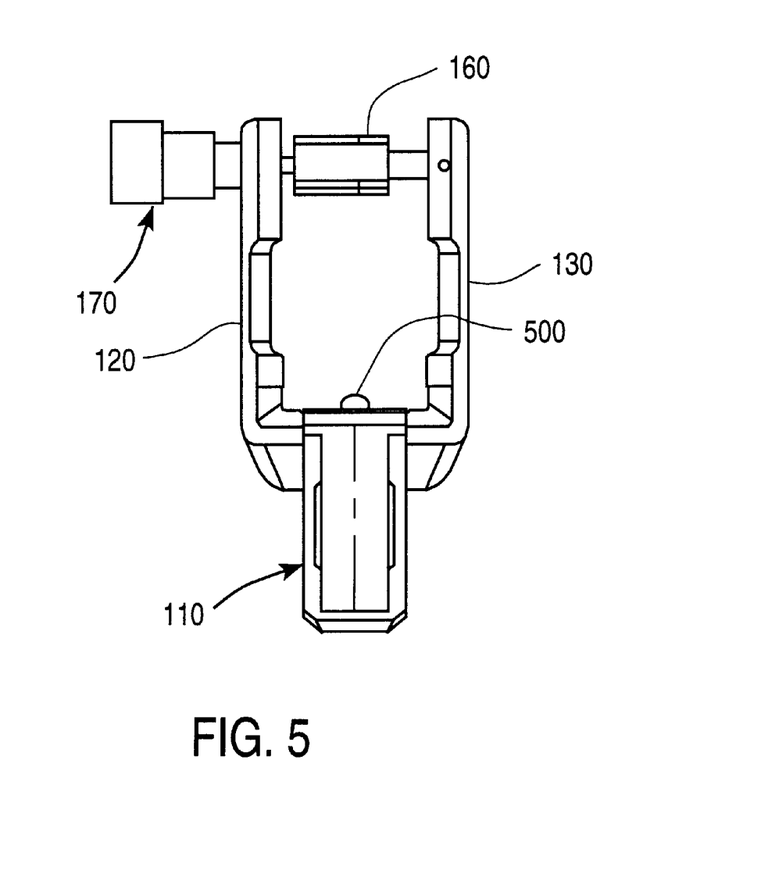
FIG. 5 is a top view of the needle guide mount shown in FIG. 1.

FIG. 5 is a view from above of the preferred embodiment of the needle guide mount according to the invention in the open position (but with the gate assembly aligned for securing in the closed position. As the figure shows, a bump or ridge or other protruding member 500 is preferably provided on the inner-facing surface of the main body 110.

FIG. 6 shows the needle guide mount 100 according to the invention mounted on a conventional transducer probe 600. The knob arm 130 has been cut away to show how the inner surface of the pivot block 160 preferably is shaped to follow the contour of the probe when the needle guide mount is properly mounted. A conventional needle guide 610 is mounted on the surface 115 of the main body 110 in any conventional manner, for example by a snap-lock arrangement. The needle guide 610 itself receives a needle 620 and guides it, usually by means a channel, into the patient's body so that the tip of the needle enters the correct region, which is imaged by the transducer probe. Signals from the probe pass by way of a cable 630 to conventional imaging equipment.

As FIG. 6 shows, the body of the probe 600 preferably has an indentation 640 that corresponds and mates with the protrusion 500 of the main body of the needle guide mount. This may also be reversed: the protrusion may be on the probe and the indentation may be on the main body. This reversed configuration would possibly allow, for example, retrofitting of a protruding portion or member onto an existing probe.

Recall that even slight angular deviation of the gate assembly from alignment with the opening 180 will prevent the user from being able to screw the knob 170 down onto the post 246 and thereby secure the mount on the probe. Either of at least two types of mounting will cause such misalignment. First, if the arms 120, 130 are mounted over the probe where the probe is too wide, then the pivot block 160 will be pushed outward, which in turn will push the gate assembly out of mounting alignment. Second, even if the probe were to be completely cylindrical, only one orientation or mounting position will allow the protrusion 500 (whether on the body or the probe) to fit into the matching indentation 640. In any other position, the protrusion will push the probe away from the main body, which will also push the pivot block outward. Even when not looking at the probe 600 and mount 100, therefore, the user will be able to feel when the mount is properly mounted because there will be no other position in which it can be secured by the knob.

Note that the pivot block 160 could be eliminated if it is known that the probe surface would extend to just touch the shaft 140 itself when the mount is properly installed. In such a case, one could also "combine" the shafts 140 and 240 into a single, uninterrupted, single or multi-diameter shaft. One could then also optionally include a groove on the rear surface (opposite the main body 110) in which the combined shaft would rest only when in the proper position. The illustrated embodiment of the invention, including the pivot block 160, with separate shafts, is preferred, however, because it allows the invention to be used for different probes by replacing one pivot block 160 with another of a different thickness and shape adapted to a different probe body.

Figure 7:
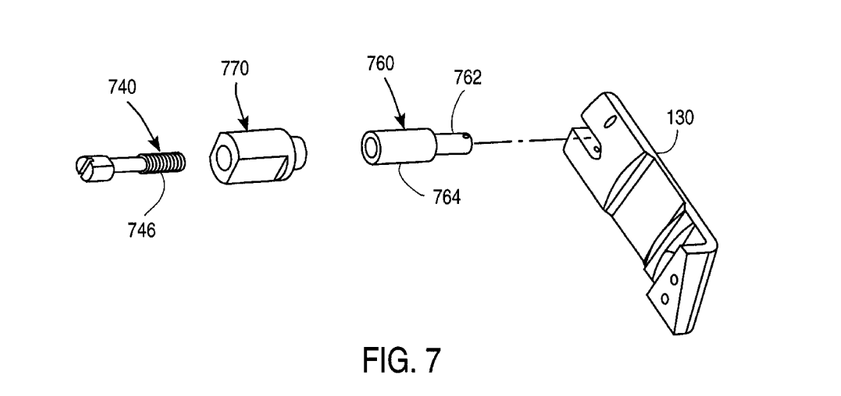
FIGS. 7 and 8 show an alternative embodiment of the invention and correspond to FIGS. 2 and 3, respectively.
Figure 8:
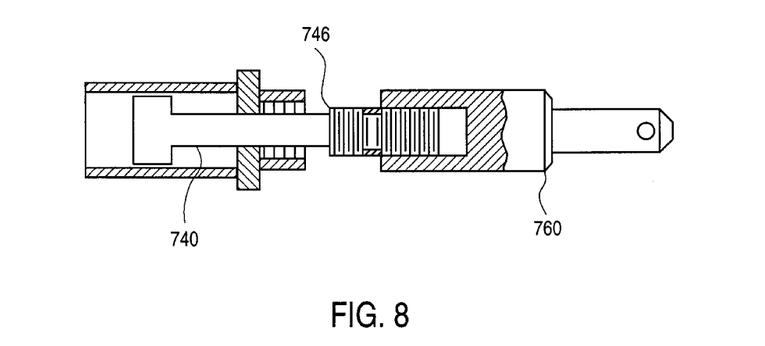

FIGS. 7 and 8 illustrate such an alternative embodiment of the invention, and are to be compared with FIGS. 2 and 3, respectively. In the illustrated alternative embodiment, the pivot block 160 on the shaft 140 has been replaced with the mainly cylindrical, contact member 760. One portion of the member 760 is a shaft 762, which corresponds to the shaft 140. Another portion of the member 760 is an internally threaded, mainly cylindrical portion 764, which makes contact with the surface of the probe in the properly mounted, closed position. The contact portion 764 may also be oblong or otherwise rounded or flattened to conform to the outer surface of the probe.

The three-portioned knob 170 is, in the alternative embodiment, replaced with a knob 740 in which the outer and middle portions have been "combined". A post member 740, which corresponds to the post member 248, extends through the knob 740 and screws or is otherwise secured in the member 760. As shown, the threaded post 746 itself serves both to secure the post member 740 in the contact member 760, and also to provide the external threading with which internal threading of the innermost position of the knob 740 mates. To make proper assembly easier, and to provide a guide as to how far into the contact member 760 the post 746 should be screwed and then secured (for example, by soldering), the post 746 may be divided into two separate threaded sections. Otherwise, normal measurement techniques may be used to ensure proper assembly, with the advantage that only a single thread need be cut or provided on the post member.

In the illustrated, preferred embodiments, the gate assembly pivots in the X-Y plane (see FIG. 1), that is, about the pivot pin 145 (see FIGS. 1 and 2), which extends vertically, that is, in the Z-direction. This has proven to be the most natural, comfortable and convenient arrangement. Depending on the shape of the probe, however, it would also be possible to mount the pivot pin and gate assembly so that the assembly pivots about the Y-axis. The opening 180 would then need to face upward or downward (rather than rearward, as in the figures), depending on which direction (from above or from below) the assembly is to swivel during mounting on the probe.

We claim:

1. A needle guide mount for mounting a needle guide on an imaging probe, comprising:

a main guide body;

a knob arm and a pivot arm each attached at one end to the main guide body;

a gate assembly pivotably mounted at a pivot point in the pivot arm;

the gate assembly having a central axis, an open position, in which the gate assembly can pivot freely away from the knob arm, and a closed position, in which the gate assembly is secured in the knob arm and further including:

a shaft;

a knob movable longitudinally and rotatably on the shaft; and locking means for permitting the gate assembly to enter the closed position only when the central axis of the gate assembly lies less than a predetermined maximum misalignment angle away from a correct mounting alignment axis.

2. A needle guide mount as in claim 1, in which the locking means comprises a threaded post member mounted on the shaft and a mating, threaded surface on an inner portion the knob, the threaded surface of the knob extending to and engaging the threaded post member only when the gate assembly lies less than the predetermined maximum misalignment angle away from the correct mounting alignment axis.

3. A needle guide mount as in claim 2, in which:

the knob arm has a substantially circular opening, the alignment axis extending substantially through a center of the opening;

the outer portion of the knob is larger than the opening;

the inner portion of the knob is no larger than the opening;

when the gate assembly is in the closed position, the outer portion seats against the knob arm and within the opening.

4. A needle guide mount as in claim 1, further including contact means mounted on the shaft for contacting an outer surface of the probe and for urging the gate assembly out of alignment with the alignment axis only when the needle guide mount is in an incorrect orientation relative to the probe.

5. A needle guide mount as in claim 1, further including a protrusion that mates with an indentation formed on the probe when the needle guide mount is in a correct orientation relative to the probe, and also forming means for urging the gate assembly out of alignment with the alignment axis by contacting a non-indented portion of the probe only when the needle guide mount is in the correct orientation.

6. A needle guide mount as in claim 1, further including an indentation receiving and mating with a protrusion formed on the probe when the needle guide mount is in a correct orientation relative to the probe, the protrusion also forming means for urging the gate assembly out of alignment with the alignment axis by contacting a non-indented portion of the needle guide mount only when the needle guide mount is in the correct orientation.

* * * * *